US009566360B2

(12) United States Patent
Morikawa et al.

(10) Patent No.: US 9,566,360 B2
(45) Date of Patent: Feb. 14, 2017

(54) FENTON REACTION CATALYST USING COFFEE GROUNDS OR TEA DREGS AS RAW MATERIAL

(75) Inventors: Claudio Kendi Morikawa, Tsu (JP); Makoto Shinohara, Tsu (JP)

(73) Assignee: INCORPORATED ADMINISTRATIVE AGENCY NATIONAL AGRICULTURE AND FOOD RESEARCH ORGANIZATION, Ibaraki (JP)

( * ) Notice: Subject to any disclaimer, the term of this patent is extended or adjusted under 35 U.S.C. 154(b) by 0 days.

(21) Appl. No.: 13/637,139

(22) PCT Filed: Oct. 25, 2010

(86) PCT No.: PCT/JP2010/068804
§ 371 (c)(1),
(2), (4) Date: Sep. 25, 2012

(87) PCT Pub. No.: WO2011/121832
PCT Pub. Date: Oct. 6, 2011

(65) Prior Publication Data
US 2013/0017270 A1    Jan. 17, 2013

(30) Foreign Application Priority Data
Mar. 31, 2010  (JP) .................................. 2010-080605

(51) Int. Cl.
| *A01N 59/00* | (2006.01) |
| *A61L 2/16* | (2006.01) |
| *A61L 2/18* | (2006.01) |
| *A61L 2/22* | (2006.01) |
| *A61L 2/232* | (2006.01) |
| *B09C 1/08* | (2006.01) |
| *C02F 1/72* | (2006.01) |
| *B09C 1/02* | (2006.01) |
| *C09K 11/07* | (2006.01) |
| *A01N 59/16* | (2006.01) |
| *B01J 31/00* | (2006.01) |
| *B01J 23/745* | (2006.01) |

(52) U.S. Cl.
CPC ................ *A61L 2/16* (2013.01); *A01N 59/16* (2013.01); *A61L 2/18* (2013.01); *A61L 2/22* (2013.01); *A61L 2/232* (2013.01); *B01J 31/00* (2013.01); *B09C 1/02* (2013.01); *B09C 1/08* (2013.01); *C02F 1/725* (2013.01); *C09K 11/07* (2013.01); *B01J 23/745* (2013.01); *C02F 2305/026* (2013.01); *Y02W 10/37* (2015.05)

(58) Field of Classification Search
None
See application file for complete search history.

(56) References Cited

U.S. PATENT DOCUMENTS

| 2,535,627 | A | 12/1950 | Earp-Thomas |
| 3,706,545 | A | 12/1972 | Gray et al. |
| 4,006,263 | A * | 2/1977 | Klug et al. ..................... 426/594 |
| 4,528,200 | A * | 7/1985 | Coleman ......................... 426/74 |
| 5,741,427 | A | 4/1998 | Watts et al. |
| 6,319,328 | B1 | 11/2001 | Greenberg et al. |
| 6,488,732 | B2 * | 12/2002 | Scanlan ............................. 71/8 |
| 7,662,294 | B1 | 2/2010 | Cox |
| 9,162,219 | B2 | 10/2015 | Morikawa et al. |
| 2002/0064567 | A1 | 5/2002 | Jassim et al. |
| 2002/0069686 | A1 | 6/2002 | Scanlan |
| 2004/0134857 | A1 | 7/2004 | Huling et al. |
| 2005/0031761 | A1* | 2/2005 | Brucker et al. ............... 426/595 |
| 2006/0035392 | A1 | 2/2006 | Funaoka et al. |
| 2006/0175266 | A1 | 8/2006 | Rima et al. |
| 2009/0188290 | A1 | 7/2009 | Marler |
| 2010/0068297 | A1 | 3/2010 | Naughton |
| 2011/0023566 | A1 | 2/2011 | Lodwig et al. |
| 2012/0285891 | A1 | 11/2012 | Lundy |
| 2014/0031196 | A1 | 1/2014 | Morikawa et al. |
| 2014/0200335 | A1 | 7/2014 | Olkowski et al. |

FOREIGN PATENT DOCUMENTS

| CA | 1032823 A1 | 6/1978 |
| CN | 101507457 A | 8/2009 |
| DE | 19628575 A1 | 1/1998 |
| DE | 19700368 A1 | 7/1998 |
| EP | 896792 A1 | 2/1999 |
| EP | 2554042 A1 | 2/2013 |

(Continued)

OTHER PUBLICATIONS

Blanchard et al. (The Journal of Physical Chemistry 1976, 80, 1362-1367).*
http://ww.nagasechemtex.co.jp/products/nousuisankinzokuen.pdf, Nagase Chemtex, pp. 1-13.
U.S. Appl. No. 13/637,193, filed Sep. 25, 2012.
International Search Report for PCT/JP2010/068804 mailed on Jan. 18, 2011.
http://is-solution.com/library/pdf/2009/s3-18.pdf, "On-site Remediation for Unsaturated Soil Layer Using Fenton's Reagent," Katsumi Nagano, Takeshi Wachi, Kusaba Shusaku, 339-342.
Database WPI Week 200962, Thompson Scientific, London, GB; AN 2009-N15720 XP002711208, abstract of CN 101507457 A (Yibin Foreign Trade Jinye Tea Co. Ltd.) Aug. 19, 2009.
Supplementary European Search Report dated Aug. 29, 2013 for EP 10849006.

(Continued)

*Primary Examiner* — Tigabu Kassa
(74) *Attorney, Agent, or Firm* — Holtz, Holtz & Volek PC

(57) ABSTRACT

A Fenton reaction catalyst including a reaction product as an active component, in which the reaction product is obtained by using roasted and ground coffee beans (in particular, coffee grounds) or tea leaves (in particular, tea dregs) as feedstocks for supplying a component having a reduction effect, and mixing the feedstocks for supplying the component having a reduction effect with an iron-supplying source containing divalent or trivalent iron in the presence of water. The Fenton reaction catalyst can be used to generate hydroxy radicals from hydrogen peroxide. The Fenton reaction catalyst can maintain iron in a divalent state for a long period of time.

6 Claims, 3 Drawing Sheets

(56) References Cited

FOREIGN PATENT DOCUMENTS

| | | | |
|---|---|---|---|
| IN | WO 2010/116379 | * | 10/2010 |
| JP | 58156539 A | | 9/1983 |
| JP | 61059248 A | | 3/1986 |
| JP | 4-114985 A | | 4/1992 |
| JP | 4-198111 A | | 7/1992 |
| JP | 06-106173 A | | 4/1994 |
| JP | 07303835 A | | 11/1995 |
| JP | 9-136807 A | | 5/1997 |
| JP | 10036681 A | | 2/1998 |
| JP | 2002-282874 A | | 10/2002 |
| JP | 2003335591 A | | 11/2003 |
| JP | 2004-249258 A | | 9/2004 |
| JP | 2004-250390 A | | 9/2004 |
| JP | 2004265622 A | | 9/2004 |
| JP | 2005087216 | * | 4/2005 |
| JP | 2006305532 A | | 11/2006 |
| JP | 2007-125521 A | | 5/2007 |
| JP | 2007-195546 A | | 8/2007 |
| JP | 2008194662 A | | 8/2008 |
| JP | 2009-062350 A | | 3/2009 |
| JP | 2009-073772 A | | 4/2009 |
| JP | 2009269843 A | | 11/2009 |
| JP | 2011211913 A | | 10/2011 |
| JP | 2012239952 A | | 12/2012 |
| PT | 0501652 A1 | | 12/2006 |
| WO | WO-2004089092 | * | 10/2004 |
| WO | WO 2007/013219 A1 | | 2/2007 |
| WO | WO 2009/140694 | * | 11/2009 |
| WO | WO 2009/140694 A2 | | 11/2009 |
| WO | WO 2009/140694 A3 | | 11/2009 |
| WO | WO 2010/116379 A2 | | 10/2010 |
| WO | 2014038596 A1 | | 3/2014 |

OTHER PUBLICATIONS

Babich, H. et al., "Mediation of the in vitro cytotoxicity of green and black tea polyphenols by cobalt chloride", *Toxicology Letters*, Elsevier Biomedical Press, Amsterdam, NL, vol. 155, No. 1, Jan. 15, 2005.

Supplementary European Search Report dated Nov. 6, 2013 for EP 10849005.

Supplementary European Search Report dated Aug. 29, 2013 for EP 108490056.

Related U.S. Appl. No. 14/915,094; First Named Inventor: Claudio Kendi Morikawa; Title: "Photocatalyst Using Reducing Organic Substance"; filed Feb. 26, 2016.

Babich, et al., "Research Strategies in the Study of the Pro-Oxidant Nature of Polyphenol Nutraceuticals", Journal of Toxicology, 2011, vol. 2011, Article ID 467305, pp. 1-12.

Kang, et al., "Enhanced chemical oxidation of aromatic hydrocarbons in soil systems", Chemosphere 61 (2005), pp. 909-922.

Li, et al., "Study on Apparent Kinetics of Photocatalytic Oxidation Degradation Rhodamine B by Photo-Fenton Reaction", Spectroscopy and Spectral Analysis, Nov. 2008, vol. 28, No. 11, pp. 2644-2648.

Ortiz De La Plata, et al., "Decomposition of 2-chlorophenol employing goethite as Fenton catalyst. I. Proposal of a feasible, combined reaction scheme of heterogeneous and homogeneous reactions", Applied Catalysis B: Environmental 95 (2010), pp. 1-13.

Savel, "Fenton reaction acceleration using maltose and ascorbic acid", Monatsschrift fur Brauwissenschaft (2003), vol. 56, No. 1-2, pp. 4-8, 2nd paragraph of '1 Introduction', '2 Experimental procedures.

Shintani, "Sterilization and Disinfection as well as Decomposition of Organic Substances in Water Through the OH Radical Generated Using Fenton Reaction and Harber-Weiss Reaction", Journal of Antibacterial and Antifugal Agents, Aug. 10, 2013, vol. 41, No. 8, pp. 433-438.

* cited by examiner

SAMPLE 1-A    SAMPLE 1-B    SAMPLE 1-C    SAMPLE 1-D (A)                    (B)

(SAMPLE 3-1)         (SAMPLE 3-2)         (SAMPLE 3-3)

(SAMPLE 4-1)　　　(SAMPLE 4-2)　　　(SAMPLE 4-3)

(SAMPLE 5-2)　　　(SAMPLE 5-1)　　　(SAMPLE 5-3)

FENTON REACTION CATALYST USING COFFEE GROUNDS OR TEA DREGS AS RAW MATERIAL

CROSS-REFERENCE TO RELATED APPLICATION

This application is a United States national phase application of International Application PCT/JP2010/068804 filed Oct. 25, 2010.

TECHNICAL FIELD

The present invention relates to a Fenton reaction catalyst including, as an active component, a reaction product obtained by using roasted and ground coffee beans (in particular, coffee grounds) or tea leaves (in particular, tea dregs) as feedstocks for supplying a component having a reduction effect, and mixing the feedstocks for supplying the component having a reduction effect with an iron-supplying source containing divalent or trivalent iron in the presence of water. Further, the present invention relates to a sterilization method, a pollutant degradation method, and a luminescence method based on chemiluminescence, which involve using the Fenton reaction catalyst to thereby generate hydroxy radicals from hydrogen peroxide.

BACKGROUND ART

The Fenton reaction is a reaction for generating hydroxy radicals by a reaction of divalent iron with hydrogen peroxide to provide strong oxidation effect. Based on the strong oxidation effect, the reaction is expected to be applied in various fields such as sterilization and degradation of harmful substances and persistent pollutants (for example, a technology for soil cleanup by injecting a Fenton reaction catalyst into soil polluted with harmful substances).

A technology for improving solubility of ferrous sulfate using citric acid or the like has been developed to catalyze the Fenton reaction (see Non Patent Literature 1). In addition, there has been reported a technology for sterilizing a mold based on the strong oxidation effect of the Fenton reaction (see Patent Literature 1). However, in the cases of such conventional Fenton catalysts, divalent iron used as a catalyst is very unstable and is inevitably oxidized into trivalent iron, resulting in losing the catalytic ability in a short time.

Therefore, there is a desire to the development of a stable Fenton reaction catalyst which can maintain the state of divalent iron, which is in nature unstable, for a long period of time.

Further, in the cases of conventional Fenton reaction catalysts, trivalent iron that is present in a large amount and can be inexpensively supplied cannot be used as an iron raw material.

CITATION LIST

Patent Literature

[PTL 1] JP 2009-062350 A

Non Patent Literature

[NPL 1] http://is-solution.com/library/pdf/2009/s3-18.pdf

SUMMARY OF INVENTION

Technical Problem

The present invention has been made in order to solve the above-mentioned problems. One object of the present invention is to develop and provide a Fenton reaction catalyst, which can maintain divalent iron stably for a long period of time.

Another object of the present invention is to produce and provide a Fenton reaction catalyst which is different from a conventional Fenton reaction catalyst in the point of capable of using trivalent iron (in expensive iron-supplying source) as divalent iron supply by reducing into divalent iron.

Solution to Problem

The inventors of the present invention have made intensive studies in view of such circumstances, and as a result, have found that the component having a reduction effect, of roasted and ground coffee or tea leaves, has an effect of stably maintaining the condition of divalent iron form, which is in nature unstable, for a long period of time. The inventors have also found that the component having a reduction effect can reduce trivalent iron into divalent iron, and can maintain divalent iron stably for a long period of time.

The present invention has been made on the basis of such findings.

That is, a first aspect of the present invention relates to a Fenton reaction catalyst including a reaction product as an active component, in which the reaction product is obtained by using roa, and ground coffee beans and/or tea leaves as feedstocks for supplying a component having a reduction effect, and mixing the feedstocks for supplying the component having a reduction effect with an iron-supplying source containing divalent or trivalent iron in the presence of water.

Further, a second aspect of the present invention relates to a Fenton reaction catalyst according to the first aspect, in which the feedstocks for supplying the component having a reduction effect are coffee grounds.

Further, a third aspect of the present invention relates to a Fenton reaction catalyst according to the first aspect, in which the feedstocks for supplying the component having a reduction effect are tea dregs.

Further, a fourth aspect of the present invention relates to a Fenton reaction catalyst according to any one of the first to the third aspects, in which the iron-supplying source is a compound which generates a divalent or a trivalent iron ion.

Further, a fifth aspect of the present invention relates to a Fenton reaction catalyst according to any one of the first to the third aspects, in which the iron-supplying source is soil, and the mixing is carried out at 40 to 200° C.

Further, a sixth aspect of the present invention relates to a Fenton reaction catalyst according to any one of the first to the fifth aspects, in which the iron-supplying source is mixed so that an iron element is contained in an amount of 0.1 to 10 parts by weight with respect to 100 parts by weight of a dried product of the feedstocks for supplying the component having a reduction effect.

Further, a seventh aspect of the present invention relates to a sanitizer including, as an active ingredient, the Fenton reaction catalyst according to any one of the first to the sixth aspects.

Further, an eighth aspect of the present invention relates to a sterilization method including using the Fenton reaction catalyst according to any one of the first to the sixth aspects to generate hydroxy radicals from hydrogen peroxide.

Further, a ninth aspect of the present invention relates to a pollutant decomposer including, as an active ingredient, the Fenton reaction catalyst according to any one of the first to the sixth aspects.

Further, a tenth aspect of the present invention relates to a pollutant degradation method including using the Fenton reaction catalyst according to any one of the first to the sixth aspects to generate hydroxy radicals from hydrogen peroxide.

Further, an eleventh aspect of the present invention relates to a luminescence method based on chemiluminescence including using the Fenton reaction catalyst according to any one of the first to the sixth aspects to generate hydroxy radicals from hydrogen peroxide.

Advantageous Effects of Invention

According to the present invention, it is possible to provide the stable Fenton reaction catalyst which can maintain divalent iron stably for a long period of time.

Further, according to the present invention, it is possible to produce the Fenton reaction catalyst which can reduce trivalent iron into divalent iron and can maintain divalent iron stably for a long period of time. As a result, it is possible to provide the Fenton reaction catalyst using an inexpensive raw material (for example, a chemical substance such as iron sulfate or iron chloride, soil, and a product obtained by dissolving metallic iron or iron sand with an acid) as an iron-supplying source.

In addition, according to the present invention, it is possible to provide the Fenton reaction catalyst more inexpensively using coffee grounds or tea dregs a the feedstocks for supplying the component having a reduction effect.

It should be noted that coffee and tea drinks are the mostly consumed beverages in the world, and the coffee grounds and tea dregs which are waste materials thereof are daily produced in large amounts throughout the world. However, the waste materials are used only in composts, deodorants, and the like, and a novel effective use method for these materials has been searched. Therefore, the present invention is expected to contribute to the effective use of these wastes, by creating a novel application method for the food waste materials.

It should be noted that the Fenton reaction catalyst of the present invention is produced using roasted and ground coffee beans or tea dregs as raw materials, and is hence highly safe for a human body and an environment.

As a result, it is possible to provide the sterilization method using the Fenton reaction catalyst according to the present invention. The Fenton reaction catalyst of the present invention is expected to diffuse in wide industrial fields. For example, the catalyst can be used in food, medicine, public health, agriculture, environmental cleanup, or the like.

In addition, according to the present invention, it is possible to provide a pollutant degradation method using the Fenton reaction catalyst.

Further, according to the present invention, it is possible to provide the luminescence method based on a luminol reaction using the Fenton reaction catalyst, and the method is expected to create a novel demand as a novel luminescence method.

DESCRIPTION OF EMBODIMENTS

Figure 1:
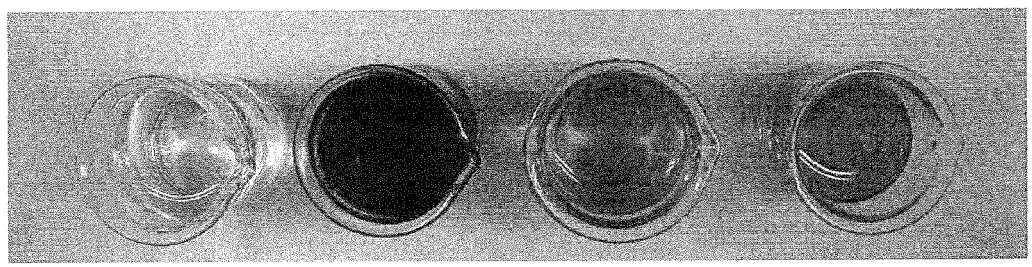
FIG. 1 A photographic image of divalent iron reduced from trivalent iron by a component derived from coffee grounds and detected by using dipyridyl in Example 1.

The present invention relates to a Fenton reaction catalyst including, as an active component, a reaction product obtained by mixing a specific feedstock for supplying a component having a reduction effect with an iron-supplying source containing divalent or trivalent iron in the presence of water.

(Feedstock for Supplying Component Having a Reduction Effect)

Roasted and ground coffee beans or tea leaves may be used as the feedstocks for supplying the component having a reduction effect of the present invention. Further, a mixture thereof may be used.

In addition, an extracted component obtained by immersing the roasted and ground coffee beans or tea leaves (in particular, coffee grounds or tea dregs) in water (so-called soluble component of coffee or tea or soluble component of coffee grounds or tea dregs) or only insoluble components (so-called coffee grounds or tea dregs) may be used as the feedstocks for supplying the component having a reduction effect. It should be noted that the components may be dried into powder before use.

The component derived from the feedstock for supplying the component having a reduction effect is a composition containing various molecular species of phenols and polyphenols, and having both an effect of reducing trivalent iron into divalent iron and an effect of maintaining divalent iron for a long period of time.

Any of coffee beans roasted and ground by a usual method may be used as the 'roasted and ground coffee beans' used in the present invention. So-called ground coffee beans are also included. Further, coffee beans which are roasted after grinding may be used.

In this case, any seeds of *Coffee* such as *Coffee arabica* (Arabica), *C. canephora* (Robusta), or *C. liberica* (Liberian coffee) may be used as the coffee beans. It should be noted that raw coffee beans, and coffee beans dried and preserved as usual may be used.

Further, from the viewpoint of the cost of raw materials, off-specification coffee beans are industrially preferably used. In particular, 'coffee grounds' wasted in large amounts after extraction of coffee are most preferably used.

It should be noted that roasting may be carried out by any of usual methods. Examples thereof include open fire roasting, hot air roasting, far-infrared roasting, microwave roasting, heated steam roasting, and low temperature roasting.

Further, grinding has only to be carried out so that usual ground coffee beans are obtained by using a coffee mill, a grinder, a stone mill, or the like, and the level of grinding widely ranges from coarsely grinding to grinding into powder. It should be noted that the grinding includes a treatment such as fracture, pulverization, or powderization. From the viewpoint of the reaction efficiency with iron, powderized coffee beans having small particle sizes are preferred.

Any picked stems and leaves of *Camellia sinensis* which is one of the tea plants may be used as the 'tea leaves' used in the present invention. Further, a method of picking the leaves may be any one, but from the viewpoint of the cost, mechanical picking is particularly preferred.

It should be noted that, in the picked tea leaves, cell contents are mixed together to cause oxidative fermentation, but tea leaves at any stage of fermentation may be used here. For example, there may be used: green tea obtained by suppressing oxidative fermentation by heating (such as green tea of middle grade, coarse green tea, twig tea, or roasted green tea); blue tea obtained by fermenting the leaves to some degree (such as oolong tea); black tea obtained by completely fermenting the leaves; and dark tea (such as pu'er tea) obtained by oxidative fermentation and fermentation with aspergilli. Preferred examples thereof include green tea, black tea, and oolong tea.

It should be noted that, from the viewpoint of the cost of raw materials, off-specification tea leaves are industrially preferably used. In particular, 'tea dregs' wasted in large amounts after extraction of tea are most preferably used.

(Iron-Supplying Source)

In the present invention, both an iron-supplying source including divalent iron and an iron-supplying source including trivalent iron may be used.

Examples of the source for supplying divalent iron include iron (II) chloride, iron (II) nitrate, iron (II) sulfate, and ion (II) hydroxide. In addition, an aqueous solution obtained by dissolving any of the compounds and containing a divalent iron ion may be used.

Examples of the source for supplying trivalent iron include: a water-soluble iron compound such as iron (III) chloride or iron (III) sulfate; an insoluble iron compound such as iron (III) oxide, iron (III) nitrate, or iron (III) hydroxide; and a natural product such as soil (in particular, iron-rich soil such as Akadama soil, Kanuma soil, or allophanic loam, or soil containing amorphous mineral (in particular, geothite)), heme iron, or seashell. Further, examples thereof include a product obtained by dis lying iron ore (natural iron ore such as pyrite, marcasite, siderite, magnetite, goethite), an iron material (metallic iron), or red soil (iron (III) oxide-rich soil such as laterite) with an acid. Further, rust may be used as a source. In addition, an aqueous solution obtained by dissolving a water-soluble iron compound and containing a trivalent iron ion may be used.

Of those, in the case where the catalyst is used in the fields of agriculture, food, medicine, and the like, an inexpensive iron compound (iron chloride or iron sulfate, irrespective of divalent or trivalent) is preferably used from the viewpoints of the cost of raw materials and stable supply.

Moreover, in the case where the catalyst is used in organic agriculture, a natural product of soil (in particular, Akadama soil, Kanuma soil, or allophanic loam) is preferably used as the iron supplying source from the viewpoints of the necessity to limit a raw material only to a natural product, cost of raw materials, and stable supply.

(Mixing Treatment)

In the present invention, when the feedstock for supplying the component having a reduction effect (or the component derived from the raw material) is mixed with the iron-supplying source (or the iron ion) and then water is added, a reaction product (active component) having an ability to catalyze a Fenton reaction can be obtained.

In this case, the expression "in the presence of water" refers to a condition where a component having a reducing power contained in the feedstock for supplying the component having a reduction effect can react with iron using water as a medium.

For example, the amount of water used may be one enough for wetting the raw materials by a mixing procedure, and is desirably, for example, 0.5 part by mass or more, preferably 2 parts by mass or more with respect to a total of 1 part by mass of the raw materials. It should be noted that the upper limit may be an amount which enables the mixing procedure, and is, for example, 100 parts by mass or less, preferably 10 parts by mass or less.

It should be noted that water may be any usual water, and examples thereof include well water, river or lake water, seawater, tap water, deionized water, and distilled water. Further, water containing a ph buffer, a salt (such as NaCl or KCl), an alcohol (such as ethanol), a saccharide, an acid, or an alkali may be used as long as the condition allows the reaction to occur.

With regard to a mixing ratio of raw materials, the iron-supplying source may be mixed in an amount of 0.1 part by weight or more, preferably 4 parts by weight or more in terms of the weight of an iron element with respect to 100 parts by weight of the dried product of the feedstocks for supplying the component having a reduction effect. If the ratio of iron is too low, iron adsorbs to the feedstocks for supplying the component having a reduction effect, which is not preferred.

In addition, the upper limit is 10 parts by weight or less, preferably 5 parts by weight or less. If the ratio of iron is too high, unreduced trivalent iron remains, which is not preferred.

In this case, with regard to a mixing procedure, mixing may be carried out simply by stirring, but may be carried out with a mixer, a large-scale stirring vessel, a Vortex mixer, a shaker, or the like.

In this case, the temperature of water may be one where water is in a liquid state (for example, 1 to 100° C.), but mixing can be carried out at about room temperature (for example, 10 to 40° C.) without particular heating.

It should be noted that, in the case where a specific natural product (specifically soil) is used as the iron-supplying source, or in the case where the iron-supplying source is mainly composed of an insoluble iron compound, it is necessary to adjust the temperature of water used in mixing to 40° C. or more, preferably 50° C. or more to facilitate the reaction between iron and the component having a reduction effect. It should be noted that the upper limit is 200° C. (in the case of heating under increased pressure), but from the viewpoint of production cost, the temperature is preferably 100° C., the boiling point of water in usual heating, or less, more preferably 70° C. or less. It should be noted that, in order to suppress thermal degradation of the component having a reduction effect under a reaction condition of 100° C. or more, it is more effective to carry out mixing in a sealed container.

With regard to a mixing time, mixing has only to be carried out for about 10 seconds or more until the component having a reduction effect is brought sufficiently into contact with iron, but in order to improve uniformity, a mixing treatment is carried out desirably for 3 minutes or more.

With regard to the upper limit, in order to prevent putrescence due to propagation of microorganisms, mixing is desirably terminated within 240 hours. However, in the case where a sterilization treatment is carried out, the upper limit is not particularly specified.

After the mixing treatment, the resultant reaction product (roasted and ground coffee or tea leaves after the mixing treatment) may be used as the Fenton reaction catalyst without additional treatments (as a product in a liquid or water-containing state) or after drying (such as natural drying or roasting). Further, a supernatant or suspension obtained by dissolving the dried product in water may be used as the Fenton reaction catalyst.

It should be noted that a liquid obtained by collecting only the supernatant from the resultant reaction product (or a dried product thereof) may be used as the Fenton reaction catalyst.

(Fenton Reaction Catalyst)

The reaction product obtained by the above-mentioned steps can maintain divalent iron stably for a long period of time, and has properties for reducing trivalent iron into divalent iron and maintaining the divalent iron stably for a long period of time.

As a result, the reaction product can maintain the activity stably for a long period of time and can be used as an excellent 'Fenton reaction catalyst.'

In this case, the Fenton reaction catalyst refers to a reaction for generating hydroxy radicals by degrading hydrogen peroxide ($H_2O_2$) by divalent iron. The generated hydroxy radicals have very strong oxidation effect and an activity of oxidatively degrading various substances.

The Fenton reaction catalyst of the present invention can maintain a stable activity, and hence can be used in various applications. For example, the catalyst may be used in sterilization, degradation of a pollutant, luminescence based on chemiluminescence, and the like.

(Sterilization Effect)

The Fenton reaction catalyst of the present invention can be used in sterilization in various applications such as medicine, food, public health, and agriculture.

The sterilization is carried out in a slightly different manner for an object to be sterilized having a solid form and an object to be sterilized having a liquid form.

In the case where the object to be sterilized has a solid form, sterilization can be carried out by preparing a solution containing the Fenton reaction catalyst and hydrogen peroxide, and, for example, spraying, applying, or kneading the solution to the object to be sterilized. It should be noted that sterilization can be carried out by immersing the object to be sterilized into the solution. Alternatively, sterilization can be carried out by applying or kneading the Fenton reaction catalyst (having a solid form) to the object to be sterilized and separately spraying hydrogen peroxide.

On the other hand, in the case where the object to be sterilized has a liquid form, sterilization can be carried out by adding and mixing the Fenton reaction catalyst (having both liquid and solid forms) and hydrogen peroxide to the object to be sterilized. It should be noted that, in the case where the Fenton reaction catalyst has a solid form, sterilization can be carried out by adding hydrogen peroxide to a liquid to be sterilized and then immersing the catalyst in it.

In the solution to be used in sterilization, the amount of the Fenton reaction catalyst used is, for example, about 0.1 to 10 g/L. Further, the amount of hydrogen peroxide used may be a very minute amount such that about 0.1 to 20 mM may be contained in the solution.

The sterilization effect is very strong, and hence a significant sterilization effect can be exerted by immersing the object to be sterilized for about several minutes, for example.

Examples of the object to be sterilized include medical equipment, walls of hospital rooms, affected areas of patients, clothes, bedclothes, lines of food manufacturing equipment, food materials, kitchen goods such as a cutting board and a kitchen knife, dishes, toilet seats, handrails, farm equipment, and plants. When the above-mentioned articles are sterilized with the Fenton reaction catalyst of the present invention, the amount of hydrogen peroxide used can be significantly reduced (by about 99 to 99.9%) compared with a usual sterilization method involving using only hydrogen peroxide.

Meanwhile, in the case where the object to be sterilized includes soil, polluted water, living bodies themselves of plants, animals, microorganisms, and the like, or organisms, sterilization can be carried out using only the Fenton reaction catalyst of the present invention (without further adding hydrogen peroxide) because hydrogen peroxide derived from the organisms has already been generated in a minute amount in the object to be sterilized.

Therefore, the Fenton reaction catalyst of the present invention can be used as an active ingredient of a sanitizer for the object to be sterilized.

Examples of the form of the sanitizer include solid and liquid forms. Examples thereof include powder, granule, sheet, board, cube, sponge, concentrate, and liquid ampule forms. Examples thereof further include a powdery form, a form of a solid mixed with an excipient or the like, a form of a capsule filled with the sanitizer, and a gel.

With regard to the form of the sanitizer used, in the case where the sanitizer is a liquid, the sanitizer is used with or without dilution, while in the case where the sanitizer is a solid, the sanitizer is dissolved in water or the like (for example, so that the solution contains the Fenton reaction catalyst at a concentration of about 0.1 to 100 g/L) or is applied or kneaded without additional treatments. It should be rioted that, in the case where the object to be sterilized has a liquid form, the sanitizer having a solid form may be added and dispersed without additional treatments.

(Pollutant Degradation Effect)

In addition, the Fenton reaction catalyst of the present invention can degrade a pollutant in polluted water or polluted soil and can be used in a step of cleanup.

Degradation of a pollutant is carried out in a slightly different manner for an object to be cleaned having a solid form and an object to be cleaned having a liquid form. In the case where the object to be cleaned has a solid form, degradation of a pollutant can be carried out by preparing a solution containing the Fenton reaction catalyst and hydrogen peroxide, and, for example, spraying, dispersing, applying, or kneading the solution to the object to be cleaned. It should be noted that degradation of a pollutant can be carried out by mixing and immersing the object to be cleaned into the solution. Alternatively, degradation of a pollutant can be carried out by applying or kneading the Fenton reaction catalyst (having a solid form) to the object to be cleaned and separately spraying hydrogen peroxide.

On the other hand, in the case where the object to be cleaned has a liquid form, degradation of a pollutant can be carried out by, for example, adding, mixing, spraying, or immersing the Fenton reaction catalyst (having both liquid and solid forms) and hydrogen peroxide into the object to be cleaned. It should be noted that, in the case where the Fenton reaction catalyst has a solid form, degradation of a pollutant can be carried out by adding hydrogen peroxide to a liquid to be cleaned and then immersing the catalyst in it.

In the solution to be used in degradation of a pollutant, the amount of the Fenton reaction catalyst used is, for example, about 0.1 to 100 g/L. Further, the amount of hydrogen peroxide used may be a very minute amount such that about 0.1 to 100 mM may be contained in the solution.

The degradation effect is very strong, and hence a significant degradation effect can be exerted by immersing the object to be cleaned for about 30 minutes, for example.

In this case, examples of the polluted water include domestic sewage, excrement water, factory effluent, and polluted river water, lake water, and seawater. Examples of the polluted soil include soil of dump sites, industrial waste, agricultural land, and old factory site.

Further, the pollutant to be degraded specifically refers to an organic compound contained in polluted water or polluted soil in nature, and examples thereof include dioxin and PCB.

It should be noted that most of the objects to be cleaned (including a microflora) already contain a minute amount of hydrogen peroxide derived from organisms. Therefore, it is possible to degrade the pollutant by using only the Fenton reaction catalyst of the present invention (without further adding hydrogen peroxide).

Therefore, the Fenton reaction catalyst of the present invention can be used as an active ingredient of a pollutant decomposer for the object to be cleaned.

Examples of the form of the pollutant decomposer include solid and liquid forms. Examples thereof include powder, granule, sheet, board, cube, sponge, concentrate, and liquid ampule forms. Examples thereof further include a powdery form, a form of a solid mixed with an excipient or the like, a form of a capsule filled with the decomposer, and a gel.

With regard to the form of the decomposer used, in the case where the decomposer is a liquid, the decomposer is used with or without dilution, while in the case where the decomposer is a solid, the decomposer is dissolved in water or the like (for example, so that the solution contains the Fenton reaction catalyst at a concentration of about 0.1 to 100 g/L) or is applied or kneaded without additional treatments. It should be noted that, in the case where the object to be cleaned has a liquid form, the decomposer having a solid form may be added and dispersed without additional treatments.

(Luminescence Effect)

Meanwhile, the Fenton reaction catalyst of the present invention can be used in luminescence based on chemiluminescence.

In this case, chemiluminescence refers to a phenomenon where a substrate is degraded by hydroxy radicals generated by the Fenton reaction to emit light. Specifically, examples thereof include chemical reactions using luminol, lophine, lucigenin, diphenyl oxalate, oxalyl chloride, and the like as luminescence substrates.

In the solution to be used in luminescence, the amount of the Fenton reaction catalyst used may be about 0.01 to 100 g/L, for example. In addition, the amount of hydrogen peroxide used may be about 0.01 to 30,000 mM. Further, the amount of luminescence substrate may be determined suitably depending on a characteristic of each substance used (in the case of luminol, about 0.1 to 10 g/L).

The Fenton catalyst is very stable, and hence can exert a luminescence effect stably for a long period of time.

The luminescence reaction can be used in illumination, electrical power generation (in combination with a solar cell), or the like.

EXAMPLES

Hereinafter, the present invention is described by way of examples, but the scope of the present invention is not limited by these examples.

Example 1

Examination of Ability to Reduce Iron of Component in Coffee Grounds

An experiment on reduction of trivalent iron into divalent iron was carried out using coffee grounds. FIG. 1 shows the results.

10 g of dried coffee grounds were added to and mixed in 50 mL of an aqueous solution of 0.1% iron (III) chloride (Sample 1-A), and the mixture was allowed to stand still at room temperature for several minutes to perform a reaction (Sample 1-B). When 0.2% dipyridyl (dipyridyl 2 g, acetic acid 100 g/L) was added to a filtrate of the reaction solution (Sample 1-C), the solution turned red, which showed the presence of divalent iron (Sample 1-D).

It should be noted that dipyridyl is a substance which turns red when reacted with divalent iron and is used for detection of divalent iron. The substance does not react with trivalent iron and remains colorless.

The results reveal that a component in the coffee grounds reduces trivalent iron into divalent iron and maintains divalent iron stably. It should be noted that chlorogenic acid, tannic acid, caffeic acid, or the like contained in coffee has been conventionally known to have an effect of improving the solubility of iron but has not been known to have an ability to reduce trivalent iron into divalent iron.

This is the first to show the component derived from the coffee grounds has an effect of reducing trivalent iron into divalent iron. It should be noted that the component having a reduction effect was considered to be any of phenols or polyphenols.

Example 2

Ability to Catalyze Fenton Reaction

The fact that a reaction product of coffee grounds and iron has an ability to catalyze the Fenton reaction was examined by a luminol reaction (a luminescence reaction caused by oxidizing luminol by generation of hydroxy radicals).

First, iron (III) chloride was added in an amount of 4 parts by weight in terms of iron element to 100 parts by weight of coffee grounds (dried product), and water was added thereto in twice the total weight of the coffee grounds and iron chloride. The mixture was allowed to stand still at room temperature for several minutes to perform a reaction. After that, the resultant product was dried by air and suspended in water so that a concentration of 1 g/L was achieved, followed by filtration.

Figure 2:
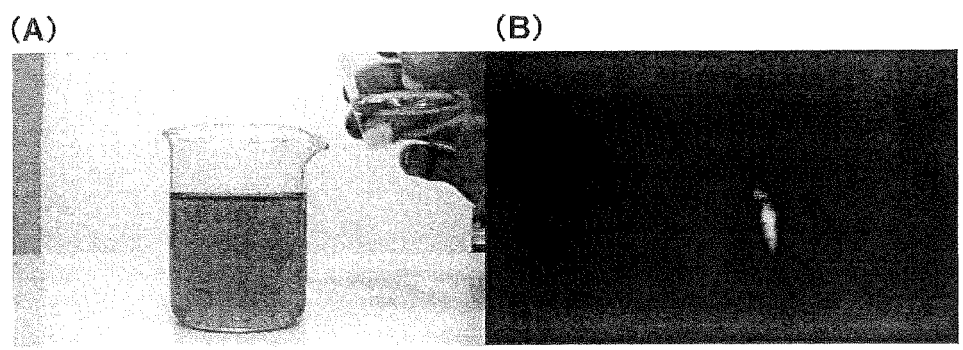
FIG. 2 Photographic images of a Fenton reaction which is catalyzed by a reaction product of coffee grounds and an iron raw material, and is detected by a luminol reaction in Example 2.

When a small amount of the resultant filtrate was added to 100 ml of a luminol solution (1 g/L luminol, 4 g/L potassium hydroxide, 0.3% hydrogen peroxide) (FIG. 2A), blue light was emitted (FIG. 2B).

The results suggest that, when the reaction product of the coffee grounds and iron is mixed with hydrogen peroxide, a Fenton reaction is catalyzed to generate hydroxy radicals.

Example 3

Sterilization Effect 1 (Sterilization of *Escherichia coli*)

The sterilization effect by the ability to catalyze the Fenton reaction of the reaction product of the coffee grounds and iron was examined for *Escherichia coli*.

A filtrate was prepared in the same way as in Example 2 by filtrating 1 g/L of the reaction product of the coffee grounds and iron, and then was added with hydrogen peroxide at a concentration of 10 mM and *Escherichia coli* at a density of $1.0 \times 10^4$ cfu/mL (Sample 3-1).

It should be noted that, as controls, *Escherichia coli* was added to the filtrate of the reaction product in the same way as above to prepare a sample (Sample 3-2), and *Escherichia coli* was added to a solution containing only hydrogen peroxide (10 mM) in the same way as above to prepare a sample (Sample 3-3).

Figure 3:
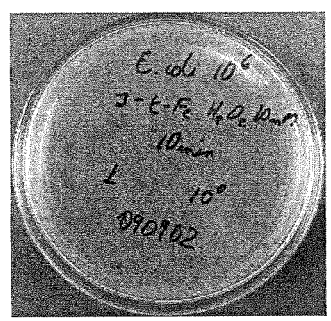
FIG. 3 Photographic images showing a sterilization effect by the Fenton reaction catalyzed by a reaction product of coffee grounds and an iron raw material in Example 3.
Figure 3:
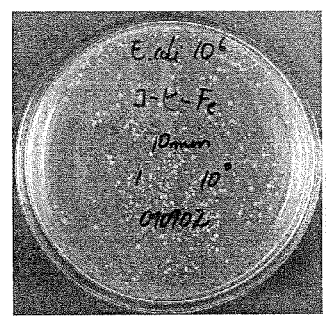
Figure 3:
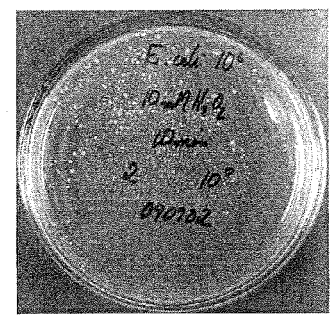

Then, 10 minutes later, 0.1 mL of each of the solutions was fractionated and plate-cultured on a TTC medium. FIG. 3 shows the results.

As a result, *Escherichia coli* in Sample 3-1 (the reaction product+hydrogen peroxide) was sterilized by a 10-minute treatment. On the other hand, in Sample 3-2 (only the reaction product) and Sample 3-3 (only hydrogen peroxide), a large amount of *Escherichia coli* survived.

This shows that, when the reaction product of the coffee grounds and iron is mixed with hydrogen peroxide, the Fenton reaction can be catalyzed to sterilize *Escherichia coli*.

Example 4

Soil-Borne Pathogen Sterilization Effect 1 (Sterilization of *Ralstonia solanacearum*)

The sterilization effect by the ability to catalyze the Fenton reaction of the reaction product of the coffee grounds and iron was examined for *Ralstonia solanacearum*.

A filtrate containing 1 g/L of the reaction product of the coffee grounds and iron was prepared in the same way as in Example 2, hydrogen peroxide was added at a concentration of 1 mM to the filtrate, and *Ralstonia solanacearum* was added thereto at a concentration of $1.0 \times 10^6$ cfu/mL (Sample 4-1). Further, as controls, *Ralstonia solanacearum* was added to a filtrate containing only the reaction product (1 g/L) in the same way as above to prepare a sample (Sample 4-2), and *Ralstonia solanacearum* was added to a solution containing only hydrogen peroxide (1 mM) in the same way as above to prepare a sample (Sample 4-3).

Figure 4:
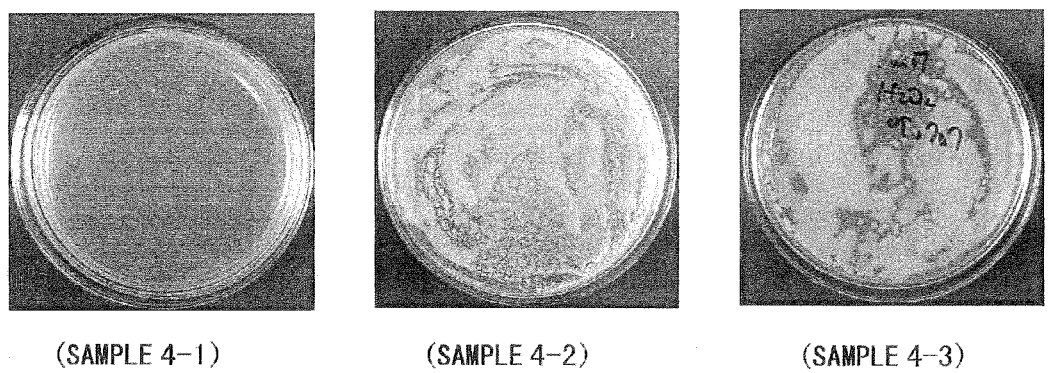
FIG. 4 Photographic images showing a sterilization effect by Fenton reaction catalyzed by a reaction product of coffee grounds and an iron raw material in Example 4.

Then, 10 minutes later, 0.1 mL of each of the solutions was fractionated and plate-cultured on a TTC medium. FIG. 4 shows the results.

As a result, *Ralstonia solanacearum* in Sample 4-1 (the reaction product+hydrogen peroxide) died by a 10-minute treatment to less than the detection limit (<10 cfu/mL). On the other hand, in Sample 4-2 (only the reaction product) and Sample 4-3 (only hydrogen peroxide), a large amount of *Ralstonia solanacearum* survived.

This shows that the Fenton reaction catalyzed by the reaction product of the coffee grounds and iron provides a strong sterilization effect on other microorganism than *Escherichia coli*.

Example 5

Examination 2 of Ability to Reduce Iron of Component in Coffee Grounds

An experiment on reduction of trivalent iron contained in Akadama soil into divalent iron was carried out using coffee grounds.

1,200 g of Akadama soil were mixed with 800 g of coffee grounds, and water was added and mixed thereto in twice the total weight of the Akadama soil and coffee grounds. The resultant was allowed to stand still at 60° C. overnight to perform a reaction. After the reaction, the resultant was dried by air. Then, 2 g of the resultant product were added to and suspended in 1 L of distilled water (Sample 5-1: coffee grounds/Akadama soil suspension). It should be noted that, as a control, 1.2 g of Akadama soil were suspended alone in 1 L of water to prepare a solution (Sample 5-2: Akadama soil suspension). The solutions were allowed to stand still at room temperature for 44 days.

Further, a solution was prepared as a comparative sample in the same manner as above except that the same weight of citric acid was used instead of the coffee grounds (Sample 5-3: citric acid/Akadama soil suspension). It should be noted that the comparative sample was not allowed to stand still at room temperature for a long period of time.

Figure 5:
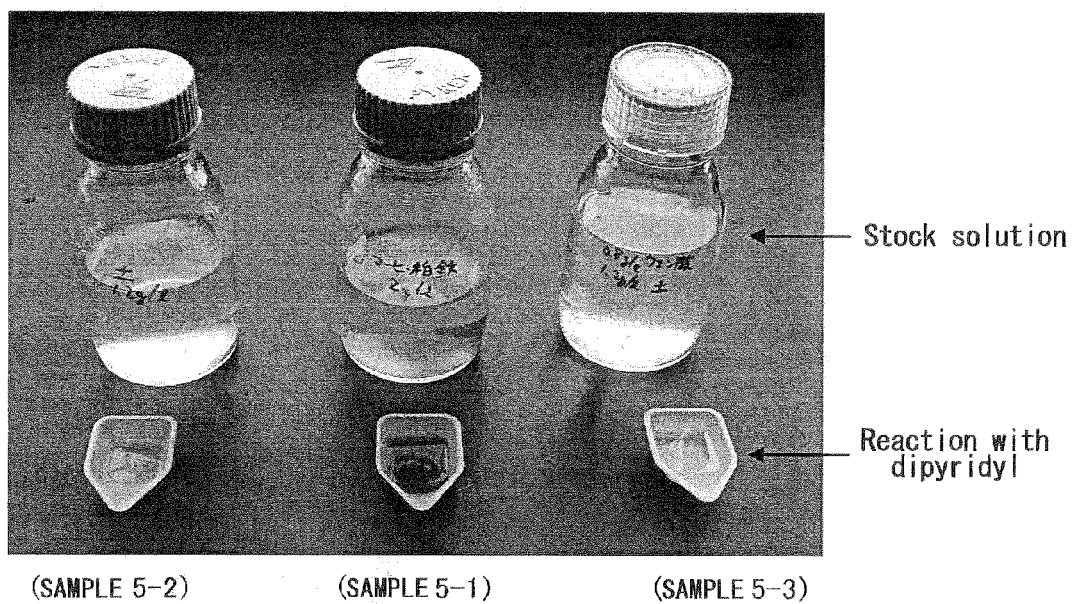
FIG. 5 A photographic image of divalent iron reduced from trivalent iron in soil by a component derived from coffee grounds and detected by using dipyridyl in Example 5.
Figure 6:
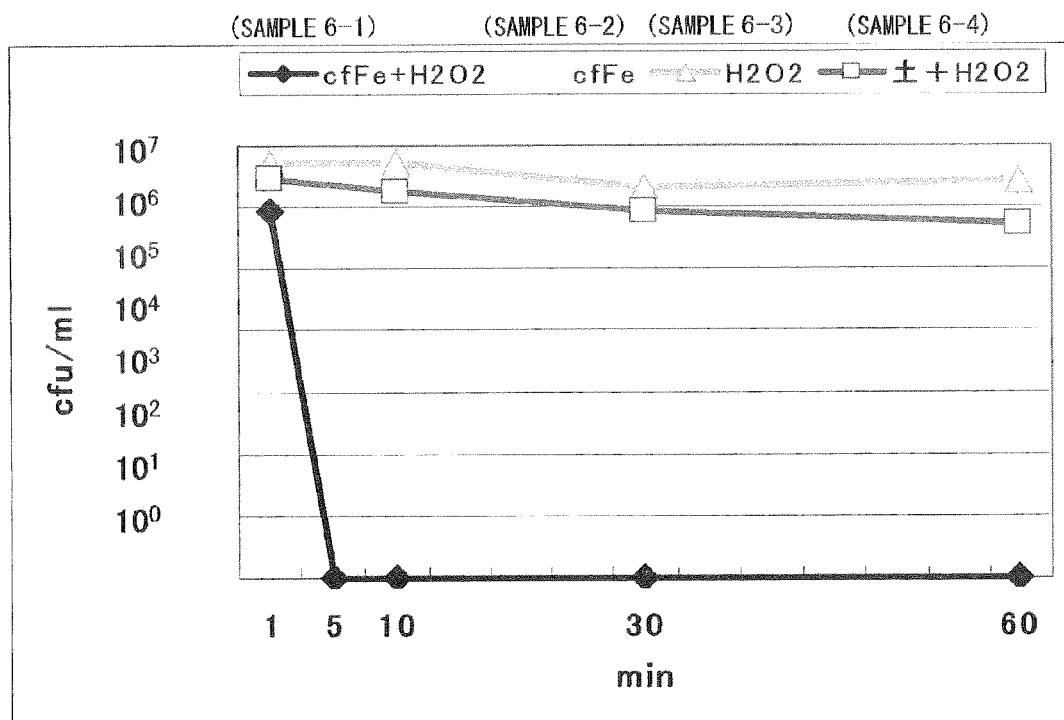
FIG. 6 A drawing illustrating the sterilization effect of a Fenton reaction catalyzed by a reaction product of coffee grounds and an iron raw material in Example 6.
Figure 7:
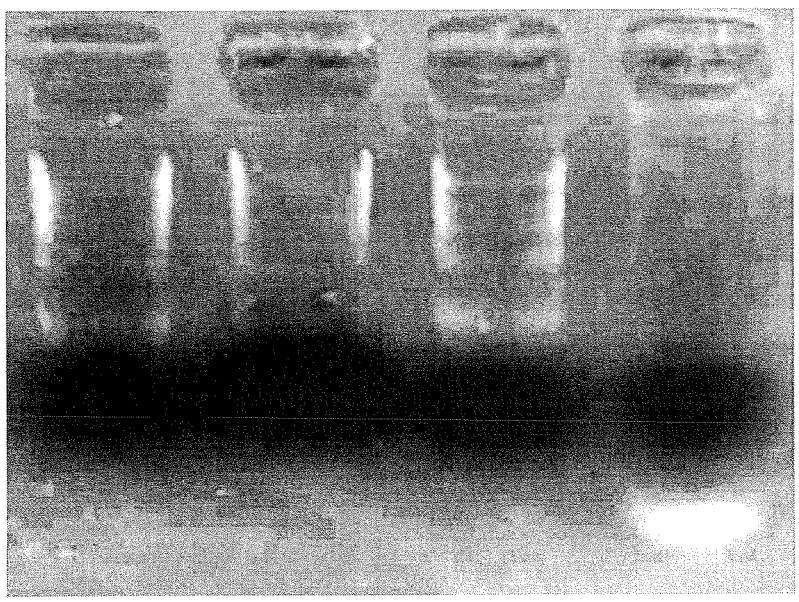
FIG. 7 A drawing illustrating a DNA degradation activity of the Fenton reaction catalyzed by a reaction product of coffee grounds and an iron raw material in Example 7.

0.1 ml of 0.2% dipyridyl (dipyridyl 2 g, acetic acid 100 g/L) was added to 3 ml of each of the resultant three solutions, and color development was observed to detect divalent iron. FIG. 5 shows the results.

As a result, divalent iron was detected from Sample 5-1 (coffee grounds/Akadama soil suspension), and the result suggested that the coffee grounds reduced trivalent iron in the Akadama soil into divalent iron and was able to maintain the state stably for a long period of time (44 days).

On the other hand, divalent iron was not detected from Sample 5-3 (citric acid/Akadama soil suspension), and the result suggested that citric acid which was known to have a strong effect of dissolving iron could not reduce trivalent iron in the Akadama soil into divalent iron (even immediately after the some production method). In addition, divalent iron was not detected from Sample 5-2 (Akadama soil suspension) as a control.

This reveals that trivalent iron in Akadama soil can also be reduced into divalent iron by using the coffee grounds and utilized.

Example 6

Soil-Borne Pathogen Sterilization Effect 2 (Examination of Sterilization Rate)

For the reaction product of the coffee grounds and iron, the rate of sterilization by the ability to catalyze a Fenton reaction was examined.

In the same manner as in Example 4, hydrogen peroxide was added at a concentration of 1 mM to a filtrate containing 1 g/L of the reaction product of the coffee grounds and iron, and *Ralstonia solanacearum* was added thereto at $1.0 \times 10^6$ cfu/mL (Sample 6-1).

Further, as controls, *Ralstonia solanacearum* was added to a filtrate containing only the reaction product (1 g/L) in the same manner as above to prepare a sample (Sample 6-2), and *Ralstonia solanacearum* was added to a solution containing only hydrogen peroxide (1 mM) in the same manner as above to prepare a sample (Sample 6-3).

It should be noted that, as a comparative experiment, *Ralstonia solanacearum* was added in the same manner as above to a product obtained by adding hydrogen peroxide at a concentration of 1 mM to an Akadama soil suspension (0.6 g/L) to prepare a sample (Sample 6-4) (note: Akadama soil was used as a raw material for supplying trivalent iron).

Then, 0.1 mL of each of the solutions was fractionated with time and subjected to dilution plating on a TTC medium, and the number of surviving *Ralstonia solanacearum* was counted. FIG. 6 illustrates the results.

As a result, in Sample 6-1 (the reaction product+hydrogen peroxide), *Ralstonia solanacearum* died in 5 minutes to less than the detection limit (<10 cfu/mL). On the other hand, in Sample 6-2 (only the reaction product) and Sample 6-3 (only hydrogen peroxide), the bacterial density changed little. Further, also in Sample 6-4 (Akadama soil suspension+hydrogen peroxid solution), the bacterial density changed little.

This suggests that the Fenton reaction catalyzed by the reaction product of the coffee grounds and iron provides a very strong sterilization effect in a very short time. In addition, it was suggested that Akadama soil used as an iron-supplying source had no ability to catalyze the Fenton reaction, and hence did not provide the sterilization effect.

Example 7

Strong Degradation Effect

For the reaction product of the coffee grounds and iron, an activity of degrading DNA by the ability to catalyze a Fenton reaction was examined.

10 μl of hydrogen peroxide (10 mM), and 10 μl, of a filtrate containing 20 g/L of a reaction product of coffee grounds and iron (prepared in the same way as in Example 2) were added to 10 μL of a commercially available λ phage DNA HindIII Marker (TAKARA BIO INC.) (Sample 7-1). In addition, as controls, only the filtrate of the reaction product was added to the DNA solution in the same way as above to prepare a sample (Sample 7-2), and only hydrogen peroxide was added to the DNA solution in the same way as above to prepare a sample (Sample 7-3).

The samples were treated at room temperature for 10 minutes. After that, the samples were subjected to agarose electrophoresis to detect DNA. FIG. 7 shows the results.

As a result, in Sample 7-1 (the reaction product+hydrogen peroxide), a ladder disappeared, which suggested that the DNA was degraded. On the other hand, in Sample 7-2 (only the reaction product) and Sample 7-3 (only hydrogen peroxide), the DNA ladder did not change.

This shows that the Fenton reaction catalyzed by the reaction product of the coffee grounds and iron has a strong DNA-degrading activity.

INDUSTRIAL APPLICABILITY

The Fenton reaction catalyst of the present invention is expected to diffuse in wide industrial fields because all raw materials of the catalyst are easily available.

The catalyst is expected to be used in sterilization in the fields of agriculture, food, medicine, and public health, for example. Further, the catalyst is expected to be used in a pollutant degradation method. In addition, when the catalyst is combined with a reaction with a chemiluminescence substance, the catalyst is expected to create a novel demand as a novel luminescence method.

Further, according to the present invention, it is expected that novel applications of food wastes such as coffee grounds and tea dregs are created to contribute to an effective use.

The invention claimed is:

1. A Fenton reaction catalyst comprising a reaction product, wherein the reaction product comprises divalent iron, wherein the reaction product is obtained by providing a feedstock for supplying a component having a reduction effect, said feedstock being selected from the group consisting of (i) coffee grounds after extraction of coffee and (ii) tea dregs, said feedstock being a dried product, and mixing said feedstock with an iron ion-supplying source containing divalent or trivalent iron, and then adding water, said source being at least one substance selected from the group consisting of iron (II) chloride, iron (III) chloride, iron (II) nitrate, iron (III) nitrate, iron (II) sulfate, iron (III) sulfate, iron (II) hydroxide, iron (III) hydroxide, iron (III) oxide; a heme iron; a product obtained by dissolving iron ore, metallic iron or iron (III) oxide-rich red soil with an acid; and rust, and wherein in the mixing, the iron ion-supplying source is mixed so that elemental iron is contained in an amount of 0.1 to 10 parts by weight with respect to 100 parts by weight of the dried product of said feedstock.

2. The Fenton reaction catalyst according to claim 1, wherein said feedstock comprises coffee grounds after extraction of coffee.

3. The Fenton reaction catalyst according to claim 1, wherein said feedstock comprises tea dregs.

4. The Fenton reaction catalyst according to any one of claims 1 to 3, wherein the mixing is carried out at a temperature of 40 to 200° C.

5. The Fenton reaction catalyst according to claim 1, wherein in the mixing, the iron ion-supplying source is mixed so that elemental iron is contained in an amount of 4 to 10 parts by weight with respect to 100 parts by weight of the dried product of said feedstock for supplying a component having a reduction effect.

6. The Fenton reaction catalyst according to claim 1, wherein the divalent or trivalent iron ion-supplying source is at least one substance selected from the group consisting of iron(II) chloride, iron(III) chloride, iron(II) nitrate, iron(III) nitrate, iron(II) hydroxide, iron(III) hydroxide, iron(III) oxide; a heme iron; a product obtained by dissolving iron ore, metallic iron or iron(III) oxide-rich red soil with an acid; and rust.

* * * * *